(12) United States Patent
Douet et al.

(10) Patent No.: US 10,831,156 B2
(45) Date of Patent: Nov. 10, 2020

(54) DEVICE AND METHOD FOR ACQUIRING A PARTICLE PRESENT IN A SAMPLE

(71) Applicants: BIOMERIEUX, Marcy-L'Etoile (FR); BIOASTER, Lyons (FR)

(72) Inventors: Alice Douet, Villebois-Lavalette (FR); Quentin Josso, Lyons (FR)

(73) Assignees: BIOMERIEUX, Marcy-L'étoile (FR); BIOASTER, Lyons (FR)

(*) Notice: Subject to any disclaimer, the term of this patent is extended or adjusted under 35 U.S.C. 154(b) by 98 days.

(21) Appl. No.: 16/095,537

(22) PCT Filed: Apr. 27, 2017

(86) PCT No.: PCT/EP2017/060027
§ 371 (c)(1),
(2) Date: Oct. 22, 2018

(87) PCT Pub. No.: WO2017/207184
PCT Pub. Date: Dec. 7, 2017

(65) Prior Publication Data
US 2019/0086866 A1    Mar. 21, 2019

(30) Foreign Application Priority Data
May 30, 2016    (EP) .................................... 16305625

(51) Int. Cl.
*G03H 1/08*    (2006.01)
*G03H 1/04*    (2006.01)
(Continued)

(52) U.S. Cl.
CPC ............. *G03H 1/0866* (2013.01); *C12Q 1/20* (2013.01); *G01N 15/1468* (2013.01);
(Continued)

(58) Field of Classification Search
None
See application file for complete search history.

(56) References Cited

U.S. PATENT DOCUMENTS
2017/0309036 A1* 10/2017 Perraut ................. G01N 21/453

FOREIGN PATENT DOCUMENTS
EP        2603601 A2      6/2013
WO    WO-2016/075279 A1  5/2016

OTHER PUBLICATIONS

Bitesizebio (https://bitesizebio.com/6938/how-to-make-the-perfect-agar-plate-every-time/, published Jul. 5, 2011 and retrieved on May 1, 2020) (Year: 2011).*

(Continued)

*Primary Examiner* — Leon Viet Q Nguyen
(74) *Attorney, Agent, or Firm* — Marshall, Gerstein & Borun LLP

(57) ABSTRACT

A device for acquisition of particles present in a sample includes a spatially coherent light source, an optical system, and an image sensor placed in the focal plane of the optical system. The image sensor is configured to capture an intensity image. A computational unit of the device is configured to construct a series of electromagnetic propagation matrices obtained for a plurality of defocusing offsets relative to a plane of focus of the optics. The computational unit is also configured to determine a first average focused electromagnetic matrix for the particles from the series of electromagnetic matrices, identifying at least one of the particles in the first electromagnetic matrix and storing the coordinates of said particle, and determining a second electromagnetic matrix at a distance of focus on a particle identified from the components of the series of electromagnetic matrices having the stored coordinates.

18 Claims, 7 Drawing Sheets

(51) Int. Cl.
  *G01N 15/14*  (2006.01)
  *G06T 7/55*  (2017.01)
  *C12Q 1/20*  (2006.01)
  *G01N 15/10*  (2006.01)
  *G01N 21/45*  (2006.01)
  *G06T 7/00*  (2017.01)

(52) U.S. Cl.
  CPC ........... G03H 1/041 (2013.01); G03H 1/0443 (2013.01); G06T 7/55 (2017.01); *G01N 21/453* (2013.01); *G01N 2015/1006* (2013.01); *G01N 2015/1454* (2013.01); *G03H 2001/0447* (2013.01); *G03H 2001/0452* (2013.01); *G06T 7/97* (2017.01)

(56) References Cited

OTHER PUBLICATIONS

International Search Report issued in PCT Patent Application No. PCT/EP2017/060027 dated Jul. 11, 2017.
Fugal et al., "Practical methods for automated reconstructions and characterization of particles in digital in-line holograms," Measurement Science and Technology, vol. 20 (2009).
Kim, Myung K., "Principles and Techniques of Digital Holographic Microscopy," SPIE Reviews, vol. 1 (2010).
Wu et al., "Three-Dimensional Identification of Microorganisms Using a Digital Holographic Microscope," Computational and Mathematical Methods in Medicine, vol. 2013 (2013).
Mallahi et al., "Automated three-dimensional detection and classification of living organisms using digital holographic microscopy with partial spatial coherent source: application to the monitoring of drinking water resources {Abstract Only}," National Center for Biotechnology Information, (2013).
Lee, Sang-Hyuk et al., "Holographic microscopy of holographically trapped three-dimensional structures," Department of Physics and Center for Soft Matter Research, vol. 15, No. 4 (2007).

\* cited by examiner

DEVICE AND METHOD FOR ACQUIRING A PARTICLE PRESENT IN A SAMPLE

TECHNICAL BACKGROUND

The present disclosure relates to the field of optical acquisition of biological particles. The biological particles may be microorganisms such as bacteria, fungi, or yeasts, for example. They may also be cells, multicellular organisms, or any other particle of contaminating particle type, dust.

The disclosed embodiments particularly advantageously apply to analyze the state of a biological particle, for example, to know the metabolic state of a bacterium after the application of an antibiotic. The disclosed embodiments for example enable to form an antibiogram of a bacterium.

BACKGROUND OF THE DISCLOSURE

An antibiogram is a laboratory technique aiming at testing the phenotype of a bacterial strain with respect to one or a plurality of antibiotics. An antibiogram is conventionally formed by culture of a sample containing bacteria and an antibiotic.

European patent application N°2 603 601 describes a method of forming an antibiogram by visualizing the state of the bacteria after a period of incubation in the presence of an antibiotic. To visualize the bacteria, the bacteria are marked with two fluorescent markers enabling to reveal their structures. The measurement of the fluorescence of the markers then enables to determine whether the antibiotic has had an efficient action on the bacteria.

However, the marking process is particularly long and complex to implement and such chemical markers have a cytotoxic effect on bacteria. As a result, such a visualization mode does not enable to observe the bacteria at several times of the culture of the bacteria.

It is thus necessary to use a sufficiently long culture time, in the order of from 24 to 72 hours, to guarantee the reliability of the measurement.

Other methods of biological particle visualization use a microscope, allowing a non-destructive measurement of a sample.

Digital holographic microscopy or DHM is an imaging technology enabling to do away with the constraints of depth of field of conventional optical microscopy. Schematically, it comprises recording a hologram formed by the interference between the light waves diffracted by the observed object and a reference wave having a spatial coherence. Such a technique is described in Myung K. Kim's article entitled "Principles and techniques of digital holographic microscopy" published in SPIE Reviews Vol. 1, Nr. 1, January 2010.

It has recently been suggested to use holographic digital microscopy to identify microorganisms in automated fashion. Thus, N. Wu et al.'s article entitled "Three-dimensional identification of microorganisms using a digital holographic microscope" published in Computational and Mathematical Methods in Medicine, Vol. 2013, art. ID Nr. 162105, describes a method of identification of different types of bacteria in the volume to be analyzed due to a digital propagation towards the plane of focus of the particle. Images focused at different depths are used to reconstruct a three-dimensional representation of the microorganisms. The latter are then classified by means of a 3D non-linear filtering.

Similarly, Ahmed El Mallahi's entitled "Automated three-dimensional detection and classification of living organisms using digital holography microscopy with partial spatial coherent source: application to monitoring of drinking water resources" published in Applied Optics, Vol. 52 Nr. 1, January 2013, describes a method comprising a first step of detection of the position of the bacteria in the volume to be analyzed, a step of focusing at different depths in the volume by means of a digital propagation, and then a classification of the bacteria based on their morphological characteristics.

The above-mentioned identification methods are however complex since they require a focusing in successive planes of focus.

On the contrary, the focusing in a single plane of focus, in other words at a single depth of analysis, is generally not sufficient to identify a type of microorganism with a low false detection rate.

The objective technical problem of the present disclosure is accordingly to observe a biological particle while limiting the acquisition time, that is, with no marking and with no accurate focusing of the optical system.

SUMMARY OF THE SPECIFICATION

To solve the technical problem, the disclosed embodiments provide a device of acquisition of a particle integrating a simple acquisition with no focusing associated with a digital reconstruction of the focusing, comprising: a first average focusing intended to detect at least one particle and a second specific focusing of a region of interest containing the particle.

For this purpose, according to a first aspect, the disclosed embodiments relate to a device of acquisition of a plurality of particles present in a sample, said acquisition device comprising:

a spatially coherent or pseudo-coherent light source directed towards a first surface of said sample;

an optical system having an optical axis and achieving the conjugation between a plane of focus and a focal plane, directed towards a second surface of said sample opposite to said first surface, and placed relative to the sample so that the particles are not in the plane of focus;

an image sensor, placed in the focal plane of the optical system and configured to acquire an intensity image formed by the interference between said light source and said sample; and a computational processing unit comprising:

a unit of digital construction of a series of electromagnetic matrices modeling, from the acquired image, the electromagnetic wave in planes parallel to the plane of focus and comprised in the sample for a plurality of offsets relative to said plane;

a unit for determining a first electromagnetic matrix at an average distance of focus on the particles from the series of electromagnetic matrices;

a unit for identifying at least one of the particles in the first electromagnetic matrix and for storing the coordinates of said particle; and a unit for determining a second electromagnetic matrix at a distance of focus on a particle identified from the components of the series of electromagnetic matrices having the stored coordinates.

The disclosed embodiments thus enable to observe phenomena similar to those described in the state of the art with no chemical marking. The focusing is digitally carried out from an out-of-focus image associated with a digital reconstruction of the focusing comprising: a first average focusing intended to detect at least one particle and a second specific focusing of a region of interest containing the particle.

As a result, the measurement instruments are simplified since it is not necessary to use highly-accurate focusing devices enabling to focus an image of a few nanometers. The acquisition time is also decreased since the focusing or the marking is no longer necessary.

Further, the marking and focusing operations are conventionally carried out manually. The disclosed embodiments also enable to limit such manual interactions during the acquisition and thus to automate the particle acquisition process. As a result, the device of acquisition of a particle present in a sample may be positioned at closest to a patient to improve the rapidity of a patient's treatment.

The conventional process to determine the antibiotics efficient on a bacterial strain comprises collecting a sample containing said strain (e.g. on a patient, an animal, a food batch, . . . ) and then of transmitting the sample to an analysis center. When the analysis center receives the sample, it first cultivates the bacterial strain to obtain at least one colony thereof, which culture lasts from 24 hours to 72 hours. It then prepares from the colony a plurality of samples comprising different antibiotics and/or different concentrations of antibiotics, and then puts the samples to incubate again. After a new culture time period also in the range from 24 to 72 hours, each sample is manually analyzed to determine whether the antibiotic has had an efficient action. The results are then transmitted back to the practitioner to apply the most efficient antibiotic and/or antibiotic concentration. The disclosed embodiments enable to totally reshape this process by displacing the analysis device close to the practitioner since a subtle manipulation by an operator is no longer necessary to perform the focusing or the marking.

Typically, the disclosed embodiments have enabled to detect the structural modifications of a bacterium in the presence of an antibiotic after an incubation of some ten minutes only, and its responsiveness after two hours (detection of the presence or of the absence of a division or of a pattern coding the division) conversely to the previously-described process, which make take several days. Indeed, the measurements being non-destructive, it is possible to perform analyses very soon in the culture process without risking to destroy the sample and thus to prolong the analysis time.

According to an embodiment, said image sensor is configured to acquire an image flow, and the processing unit is configured to track a particle in the flow of first electro-magnetic matrices.

This embodiment enables to track a particle on a plurality of successive images to form a film showing the behavior of a particle over time. The conventional chemical marking method does not enable to show the behavior of a particle over time since the particles are altered after the first analysis.

The conventional method of visualization of biological particles using conventional (non-holographic) microscopy enables to show a particle over time but it requires a manual focusing for each image. Indeed, a particle is not fixed in a sample and it may displace in the plane of the support or across the sample depth. Even if a particle only displaces in the plane of its support, the focusing on the particle may be faulty between two images due to an unevenness of the support.

This embodiment enables to show a particle over time by searching a focusing capable of varying according to the support plane or across the sample depth. Advantageously, the particles are microorganisms and the duration between two acquired images originating from said image sensor is shorter than or equal to 1 minute.

Typically, this embodiment has enabled to observe the cellular division of a bacterium.

As a result, this embodiment enables to increase the reliability and the rapidity of analysis of the state of a particle. Indeed, instead of analyzing a particle only according to its physiological characteristics, it is possible to study a particle according to its behavior. For example, it is possible to observe that a bacterium no longer divides when an efficient antibiotic is present in the sample.

According to an embodiment, said series of electromagnetic matrices is obtained by a model of digital propagation of light through said sample, the electromagnetic matrices varying by modulating a distance to an optical axis of said propagation model. This embodiment enables to efficiently reconstruct the image of the particle.

Advantageously, the processing unit comprises a unit for transforming the electro-magnetic matrices originating from the propagation model by a surjective application from the complex space into the real space. The obtained matrices provide a visualization directly understandable by an operator as well as the implementation of a conventional image processing for example based on the particle morphology.

According to an embodiment, the first electromagnetic matrix is obtained by representing, for each coordinate, the components at said coordinate of the electromagnetic matrices according to said distance to said optical axis, and by searching for an average of the maximum values of all representations. This embodiment enables to efficiently detect the average focused matrix.

According to an embodiment, the second electromagnetic image is obtained by representing, for each coordinate of the identified particle, the components at said coordinate of the electromagnetic matrices according to said distance to said optical axis, and by searching for an average of the maximum values of all representations. This embodiment enables to efficiently detect the matrix focused on the particle.

According to an embodiment, the matrices of said series of electromagnetic matrices used to determine said first electromagnetic matrix and/or to determine said second electromagnetic matrix are sub-sampled according to said distance. This embodiment enables to limit the calculation time necessary for focusings.

According to an embodiment, said device comprises a plurality of acquisition units, each acquisition unit comprising an image sensor and specific focusing means, said device being configured to represent an image of a particle of each sample. This embodiment enables to make fast comparisons between a plurality of samples, for example, to form an antibiogram.

This first aspect may also be formulated in the form of a method of acquisition of a plurality of particles present in a sample, said acquisition method comprising the steps of:

emitting a spatially coherent or pseudo-coherent light source directed towards a first surface of said sample;

acquiring by means of an image sensor an intensity image, said sensor being placed in the focal plane of an optical system having an optical axis and performing the conjugation between a plane of focus and the focal plane, directed towards a second surface of said sample opposite to said first surface, and placed relative to the sample so that the particle is not in the plane of focus, the image being formed by interference between said light source and said sample;

digitally constructing a series of electromagnetic matrices modeling, from the acquired image, the electromagnetic wave in planes parallel to the plane of focus and comprised in the sample for a plurality of offsets relative to said plane;

identifying at least one of the particles in the first electromagnetic matrix and storing the coordinates of said particle; and determining a second electromagnetic matrix at a distance of focus on a particle identified from the components of the series of electromagnetic matrices having the stored coordinates.

According to a second aspect, the disclosed embodiments also aim at a method of analyzing at least one particle present in a sample, said analysis method comprising the steps of:

emitting a spatially coherent or pseudo-coherent light source directed towards a first surface of said sample;

acquiring by means of an image sensor an intensity image, said sensor being placed in the focal plane of an optical system having an optical axis and performing the conjugation between a plane of focus and the focal plane, directed towards a second surface of said sample opposite to said first surface, and placed relative to the sample so that the particle is not in the plane of focus, the image being formed by interference between said light source and said sample;

digitally constructing a series of electromagnetic matrices modeling, from the acquired image, the electromagnetic wave in planes parallel to the plane of focus and comprised in the sample for a plurality of offsets relative to said plane;

obtaining an electromagnetic matrix at a distance of focus on the particle from the series of electromagnetic matrices; and determining a state of said particle according to the electromagnetic matrix at the distance of focus on the particle.

According to this second aspect, the disclosed embodiments also enable to observe phenomena similar to those described in the state of the art with no chemical marking.

The focusing is digitally performed from an out-of-focus image associated with a digital reconstruction of the focusing. Eventually, the state of the particle is determined from the focused image. As a result, the measurement instruments are simplified since it is not necessary to use highly-accurate focusing devices enabling to focus an image of a few nanometers. The acquisition time is also decreased since the focusing or the marking is no longer necessary.

Further, the marking and focusing operations are conventionally carried out manually. According to this second aspect, the disclosed embodiments also enable to limit such manual interactions during the acquisition and thus to automate the particle analysis process. As a result, the method of analysis of a particle present in a sample may be carried out at closest to a patient to improve the rapidity of a patient's treatment.

According to an embodiment, the step of obtaining the electromagnetic matrix at the distance of focus on the particle comprises the steps of:

determining a first electromagnetic matrix at an average distance of focus on the particles from the series of electromagnetic matrices;

identifying the particle in the first electromagnetic matrix and storing the coordinates of said particle; and determining the electromagnetic matrix at a distance of focus on the particle from the components of the series of electromagnetic matrices having the stored coordinates.

This embodiment enables to efficiently determine a focused matrix of said particle by means of a first average focusing intended to detect at least one particle and of a second specific focusing on the particle.

According to an embodiment, said step of determining a state of said particle comprises the steps of:

rotating the electromagnetic matrix at the distance of focus on the particle to align the particle with a predefined axis, and calculating a distribution of the matrix aligned along said predefined axis.

This embodiment enables to do away with the orientation and the position of the particle. Further, the distribution enables to categorize the shape of the particle.

According to an embodiment, the steps of acquisition of a holographic image until the step of obtaining a focused image of a particle are carried out over time for a plurality of images, the step of determining a state of said particle being carried out according to a time variation of said particle.

This embodiment enables to show a particle over time by searching for a focusing capable of varying according to the support plane or across the sample depth. Advantageously, the time period between two images originating from said image sensor is shorter than or equal to 1 minute in the case of microorganisms, in particular of bacteria.

According to an embodiment, said step of determining a state of said particle comprises the steps of:

rotating, for each acquired image, the electromagnetic matrix at the distance of focus on the particle to align the particle with a predefined axis, and calculating, for each acquired image, a distribution of the matrix aligned along said predefined axis; and forming a matrix representation of the distributions associated with each image over time.

This embodiment enables to improve the particle categorization.

According to an embodiment, said step of determining a state of said particle is carried out according to a division state of said particle.

This embodiment for example enables to detect whether a bacterium is in a division cycle or whether an inhibitor blocks the division cycle.

According to an embodiment, said step of determining a state of said particle is carried out according to a morphological characteristic of said particle, for example, the length.

According to an embodiment, said step of determining a state of said particle is carried out according to a physiological characteristic of said particle, for example, the nuclear number.

According to an embodiment, said particle corresponds to a bacterium and said sample integrates an antibiotic.

This second aspect may also be formulated in the form of a device of acquisition of at least one particle present in a sample, said acquisition device comprising:

a spatially coherent or pseudo-coherent light source directed towards a first surface of said sample;

an optical system having an optical axis and performing the conjugation between a plane of focus and a focal plane, directed towards a second surface of said sample opposite to said first surface, and placed relative to the sample so that the particles are not in the plane of focus;

an image sensor, placed in the focal plane of the optical system and configured to acquire an intensity image formed by the interference between said light source and said sample; and a computational processing unit comprising:

a unit of digital construction of a series of electromagnetic matrices modeling, from the acquired image, the electromagnetic wave in planes parallel to the plane of focus and comprised in the sample for a plurality of offsets relative to said plane;

a unit for obtaining an electromagnetic matrix at a distance of focus on the particle from the series of electromagnetic matrices;

a unit for identifying at least one of the particles in the first electromagnetic matrix and for storing the coordinates of said particle; and a unit for determining a state of said particle according to the electromagnetic matrix at the distance of focus on the particle.

BRIEF DESCRIPTION OF THE DRAWINGS

The way to implement the presently described embodiments, as well as the resulting advantages, will better appear from the description of the following non-limiting embodiment, given as an indication, based on the accompanying drawings, where

FIG. 1: a simplified cross-section view of a device of acquisition of a particle present in a sample according to an embodiment;

FIG. 2: a simplified representation of a flowchart of the operation of a processing unit of FIG. 1 according to a first embodiment;

FIG. 3: a simplified representation of a flowchart of the operation of the average focused image determination unit of FIG. 2;

FIG. 4: a simplified representation of a flowchart of the operation of the unit for determining a region of interest of FIG. 2;

FIG. 5: a simplified representation of a flowchart of the operation of a processing unit of FIG. 1 according to a second embodiment;

FIG. 6: a simplified representation of a flowchart of the operation of the particle state prediction unit of FIG. 5;

DETAILED DESCRIPTION OF THE SPECIFICATION

Figure 1:
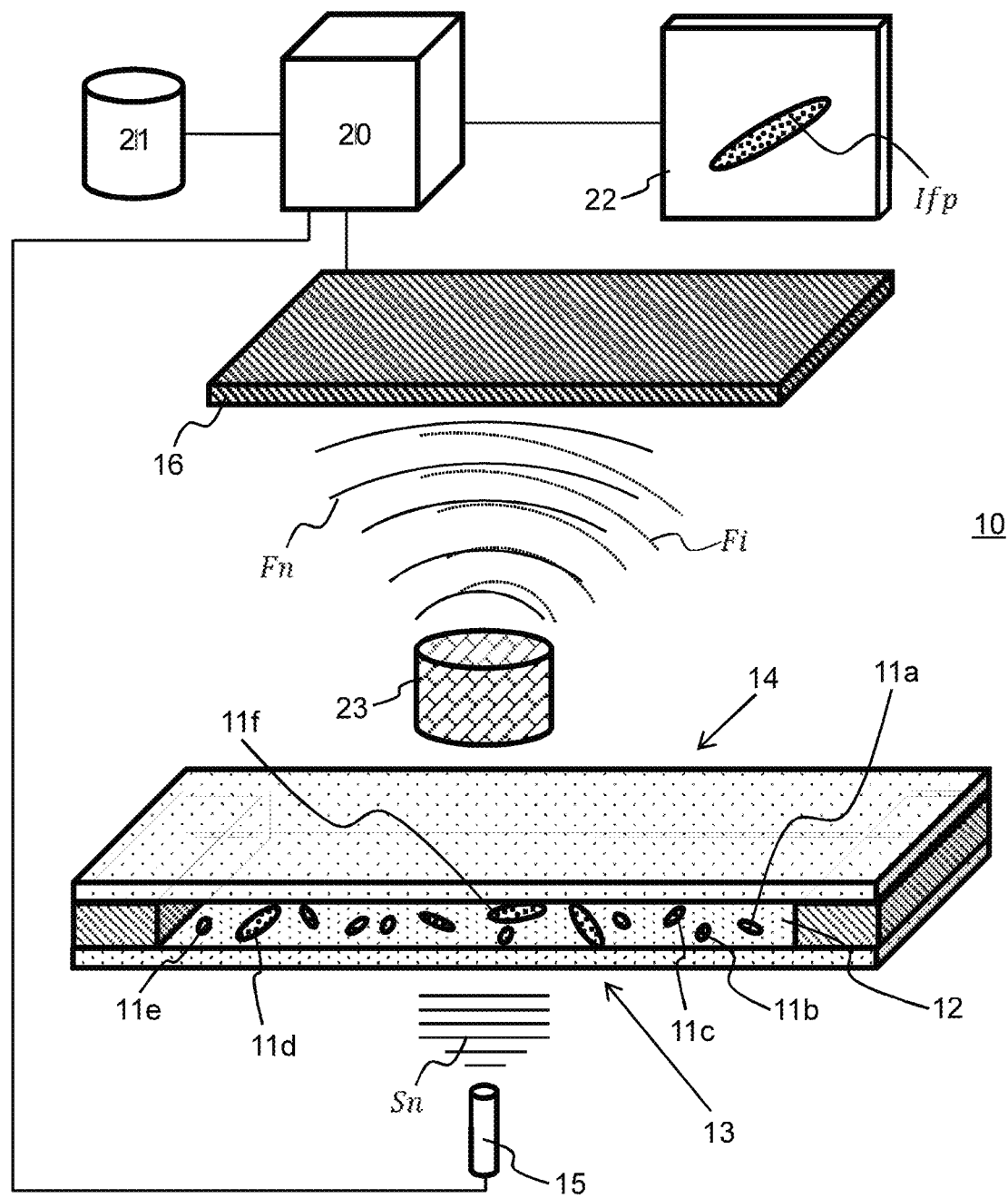
FIGS. 1 to 6 show.

FIG. 1 illustrates a device 10 for observing a particle 11a-11f present in a sample 12. Sample 12 is arranged between a light source 15 which is spatially and temporally coherent (for example a laser) or pseudo-coherent (for example, a light-emitting diode, a laser diode), and a digital sensor 16 sensitive in the spectral range of the light source. Preferably, light source 15 comprises a small spectral width, for example, smaller than 200 nm, smaller than 100 nm, or smaller than 25 nm. In the following, reference is made to the central emission wavelength of the light source, for example, in the visible range. Light source 15 emits a coherent signal Sn directed towards a first surface 13 of the sample, for example, conveyed by a waveguide such as an optical fiber.

Sample 12 is a liquid such as water, a buffer solution, a culture medium or a reactive medium (comprising or not an antibiotic), containing the particles 11a-11f to be observed. As a variation, sample 12 may appear in the form of a solid medium, preferably translucent, such as an agar-agar gelose, containing particles 11a-11f. Sample 12 may also be a gaseous medium. Particles 11a-11f may be located within the medium or at the surface of sample 12.

Particles 11a-11f may be microorganisms such as bacteria, fungi, or yeasts. They may also be cells, multicellular organisms, or any other particle of contaminating particle type, dust. The size of the observed particles 11a-11f varies from 500 nm to several hundreds of µm, or even of a few millimeters.

Sample 12 is contained in an analysis chamber, vertically delimited by a lower plate and an upper plate, for example, conventional microscope plates. The analysis chamber is laterally delimited by an adhesive or by any other tight material. The lower and upper plates are transparent to the wavelength of light source 15, the sample and the chamber for example giving way to more than 50% of the wavelength of the light source under a normal incidence on the lower plate.

Preferably, particles 11a-11f are arranged in sample 12 at the level of the upper plate. The lower surface of the upper plate comprises for this purpose ligands enabling to bind the particles, for example, polycations (e.g. poly-L-lysine) in the case of micro-organisms. This enables to contain the particles within a thickness equal to or close to the depth of field of the optical system, that is, within a thickness smaller than 1 mm (e.g. tube lens), and preferably smaller than 100 µm (e.g. microscope lens). Particles 11a-11f may however displace in sample 12.

Preferably, the device comprises an optical system 23 for example formed of a microscope lens and of a tube lens, arranged in the air and at a fixed distance from the sample. Optical system 23 is optionally equipped with a filter capable of being located in front of the lens or between the lens and the tube lens. Optical system 23 is characterized by its optical axis, its object plane, also called plane of focus, at a distance from the lens, and its image plane, conjugate of the object plane relative to the optical system. In other words, an object located in the object plane has a corresponding sharp image of this object in the image plane, also called focal plane. The optical properties of system 23 are fixed (e.g. fixed focus optics) The object and image planes are orthogonal to the optical axis.

Image sensor 16 is located, opposite a second surface 14 of the sample, in the focal plane or close thereto. The sensor, for example, a CCD or CMOS sensor, comprises a periodic two-dimensional grating of sensitive elementary sites, and a proximity electronic system which sets the exposure time and the resetting of the sites, in a way known per se. The output signal of an elementary site is a function of the quantity of radiation of the spectral range incident on said site during the exposure time. This signal is then converted, for example, by the proximity electronic system, into an image point or "pixel" of a digital image. The sensor thus generates a digital image in the form of a matrix of C columns and L rows. Each pixel of this matrix, of coordinates (c,l) in the matrix, corresponds in a way known per se to a position of Cartesian coordinates (x(c,l),y(c,l))) in the focal plane of optical system 23, for example, the position of the center of the elementary sensitive site of rectangular shape.

The pitch and the filling factor of the periodic grating are selected to respect the Shannon-Nyquist criterion regarding the size of the observed particles, to define at least two pixels per particle. Thus, image sensor 16 acquires a transmission image of the sample in the spectral range of the light source.

The image Ih acquired by image sensor 16 comprises holographic information since it results from the interference between a wave Fi diffracted by particles 11a-11f and a reference wave Fn having crossed the sample without having interacted therewith. It can of course be understood, as described hereabove, that in the case of a CMOS or CCD sensor, the digital image Ih acquired and stored in unit 20 is an intensity image, the phase information being thus here coded in intensity, with Ih according to relation:

$$Ih = \begin{pmatrix} ih(1,1) & \ldots & ih(c,1) & \ldots & ih(C,1) \\ \vdots & \ddots & \vdots & \ldots & \vdots \\ ih(1,l) & \ldots & ih(c,l) & \ldots & ih(C,l) \\ \vdots & \ddots & \vdots & \ddots & \vdots \\ ih(1,L) & \ldots & ih(c,L) & \ldots & ih(C,L) \end{pmatrix}$$

As a variation, it is possible to divide the coherent signal Sn originating from light source 15 into two components, for example, by means of a beam splitter. The first component is then used as a reference wave and the second component is diffracted by sample 12, the image in the image plane of optical system 23 resulting from the interference between the diffracted wave and the reference wave.

The intensity image Ih acquired by image sensor 16 is not focused on the particle to be observed and the obtaining of information focused on the particle is digitally achieved by a processing unit 20 connected to image sensor 16 to receive the images acquired by the latter.

"Out of focus" here means that there is no intersection between the plane of focus and the particle which is to be observed.

Processing unit 20 may correspond to a computer, a microcontroller, a touch tablet or a smart phone, or generally any computer system based on a processor capable of receiving data, processing the data by implementing computational instructions stored in a computer memory, and of delivering and/or storing in a computer memory the result of the processing. Processing unit 20 may be connected in wired or wireless fashion to image sensor 16 or by means of a wireless communication. The unit may be associated with a screen to display intermediate or final results of the method.

Figure 2:
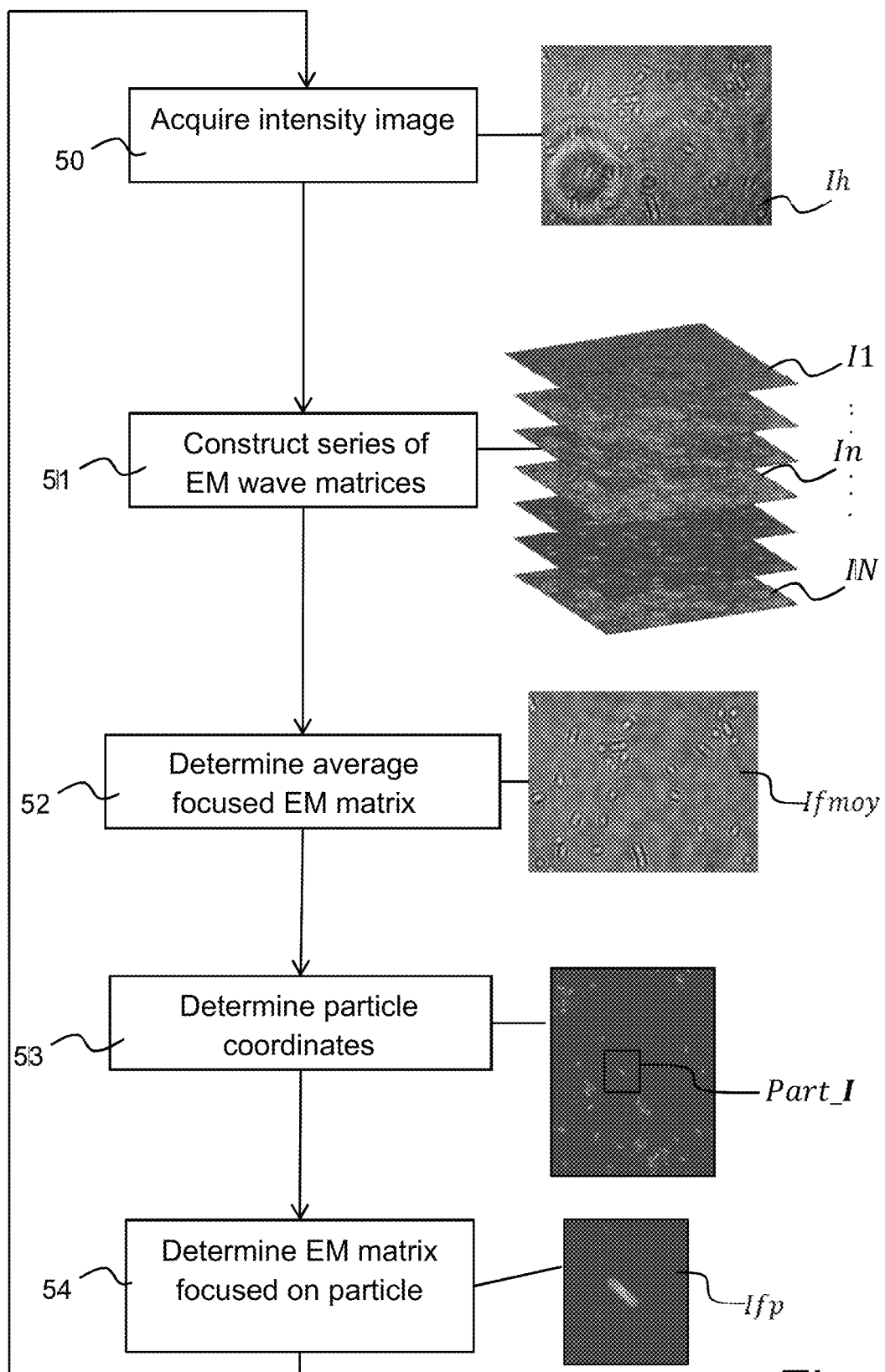

FIG. 2 illustrates computer processing units 51-53 integrated in processing unit 20 in the form of computer instructions implemented by the computer, after the acquisition 50 of intensity image Ih by image sensor 16.

A first unit 51 constructs a series of complex matrices I1, . . . , In, . . . , IN, called "electromagnetic matrices" EM, modeling from image Ih the light wave front propagated along the optical axis by a plurality of offsets relative to the plane of focus of optical system 23, and in particular the offsets positioned in the sample.

A method of calculating wave fronts by digital propagation is explained in Sang-Hyuk Lee et al.'s article entitled "Holographic microscopy of holographically trapped three-dimensional structures" published in Optics Express, Vol. 15; Nr. 4, Feb. 19, 2017, pp. 1505-1512.

More particularly, noting $h_z(r)$ the Rayleigh-Sommerfeld propagation function, that is:

$$h_z(r) = -\frac{1}{2\pi} \frac{\partial}{\partial z} \frac{e^{ikR}}{R}$$

where:
z is the so-called "defocusing" height, in other words the distance relative to the plane of focus,
$r=(|r|,\theta)$ is the position in polar coordinates in the image plane, of radial coordinate $|r|$ and of angular coordinate,
$R^2=|r|^2+z^2$, and
$k=2\pi n/\lambda$ is a wave number relative to the propagation medium of refraction index n at wavelength $\lambda$ of the light source.

Based on this relation, electromagnetic wave $a(r,z)$, of amplitude $|a(r,z)|$ and of phase $\varphi(r,z)$, in ordinate plane z may be expressed as:

$$a(r,z) = |a(r,z)|\exp(i\varphi(r,z))$$
$$a(r,z) = \frac{1}{4\pi^2}\int_{-\infty}^{+\infty} B(q)H_{-z}(q)\exp(iqr)d^2q$$

where
b(r) is the measured intensity, i.e. image Ih (the intensity of the reference wave is here assumed to be constant),
B(q) is the Fourier transform of b(r),
$H_{-z}(q)$ is the Fourier transform of $h_{-z}(r)$, and
q is the dual variable of r in the Fourier transform.

The above equations define an analytic formulation of amplitude $a(r,z)$. Although this model is developed for a propagation in a homogeneous medium (and thus with no modification of the wave number, without the presence of an interface creating a reflection and/or a deviation of the wave, etc.), and accordingly with no relation with the sample and the enclosure (which comprise many interfaces and changes of index, for example), the inventors have noted that it enables to reconstruct rich electromagnetic information in relation with the observed particles, as will be described hereafter. Thus, advantageously, processing unit 20 stores a single wave number, common for all the involved mediums, for example, the index of air. As a variation, unit 20 stores the refraction indexes of the different involved mediums along the optical axis and constructs matrices I1-IN from close to close to take into account the phenomena at the interfaces.

For bacteria, the sampling pitch in the z direction is preferably smaller than one tenth of the thickness of the bacterium, for example, smaller than 0.1 μm, and preferably smaller than 0.03 μm.

It can thus be understood that a stack of electromagnetic matrices I1-IN can be constructed for ordinates $z_1, z_2, \ldots, z_n, z_N$ along the optical axis, the origin of ordinates (z=0) being taken at the axial focusing position, each matrix In being defined by a complex amplitude $a(r,z_n)$ according to relations:

$$\begin{pmatrix} a(1,1)_{z_n} & \ldots & a(c,1)_{z_n} & \ldots & a(C,1)_{z_n} \\ \vdots & \ddots & \vdots & \ldots & \vdots \\ a(1,l)_{z_n} & \ldots & a(c,l)_{z_n} & \ldots & a(C,l)_{z_n} \\ \vdots & \ddots & \vdots & \ddots & \vdots \\ a(L,1)_{z_n} & \ldots & a(c,L)_{z_n} & \ldots & a(C,L)_{z_n} \end{pmatrix}$$

$$\forall (c,l) \in [1,C] \times [1,L]: a(c,l)_{z_n} = a(r((c,l), y(c,l), z_n))$$

Processing unit 20 then calculates on each matrix In a positive surjective application AS from the complex space $\mathbb{C}^{C \times L}$ to the real space $\mathbb{R}^{C \times L}$:

$$AS(In) = \begin{pmatrix} AS(a(1,1)_{z_n}) & \ldots & AS(a(c,1)_{z_n}) & \ldots & AS(a(C,1)_{z_n}) \\ \vdots & \ddots & \vdots & \ldots & \vdots \\ AS(a(1,l)_{z_n}) & \ldots & AS(a(c,l)_{z_n}) & \ldots & AS(a(C,l)_{z_n}) \\ \vdots & \ddots & \vdots & \ddots & \vdots \\ AS(a(L,1)_{z_n}) & \ldots & AS(a(c,L)_{z_n}) & \ldots & AS(a(C,L)_{z_n}) \end{pmatrix}$$

For example, unit 20 calculates the Hermitian norm (or its square) of the components $a(c,l)_{z_n}$, the absolute value or the square of the imaginary part (noted $Im(a(c,l)_{z_n})$ or of the real part (noted $Re(a(c,l)_{z_n})$) of the components $a(c,l)_{z_n}$, or $Re^2(a(c,l)_{z_n})+Im^2(a(c,l)_{z_n})$ or $(Re^2(a(c,l)_{z_n})+Im^2(a(c,l)_{z_n}))^{1/2}$.

Without being bound by theory, matrices AS(I1)-AS(IN) do not necessarily represent a light intensity, but the inventors have noted their resemblance with intensity images obtained under a non-coherent illumination. Particularly, the particles are represented, as in a photograph, in their particle form.

It is thus possible to apply any type of conventional image processing (segmentation, thresholding, detection of particles based on their morphology, etc.), and even for an operator to identify with the naked eye the particles (conversely to an image coding interferences which are coded in intensity in the form of fringes). In the following, to simplify the notations, matrices AS(I1)-AS(IN) are noted 1-IN, and notation $a(c,l)_{z_n}$ corresponding to $AS(a(c,l)_{z_n})$.

The method then comprises identifying particles in the sample according to the matrices I1-IN, and for each identified particle, determining an optimum distance of focus z for this particle, and then determining in the matrix of the series I1-IN corresponding to this distance, a set of pixels belonging to this particle.

Second unit 52 aims at determining an average distance of focus zfmoy from the series of matrices I1-IN and at selecting in this series the matrix, noted Ifmoy, having its distance z equal or the closest to distance zfmoy. As a variation, unit 20 recalculates matrix Ifmoy, for distance zfmoy. Average focusing distance zfmoy is that which best corresponds to the ideal conditions of focusing on the set of particles 11a-11f in the sense of a predetermined focusing criterion. This distance can be determined by all known techniques of signal processing or in the field of photography, for example, of autofocus. The resulting electromagnetic matrix Ifmoy is sufficiently "focused" to be able to detect particles at different depths in matrix Ifmoy. The detected particles are particularly those comprised in a depth of the sample equal to the depth of field. As previously described, in a preferred embodiment, the particles are arranged in a volume having a thickness close or equal to this depth of field, so that all or almost all the particles of the sample can be detected in matrix Ifmoy.

Figure 3:
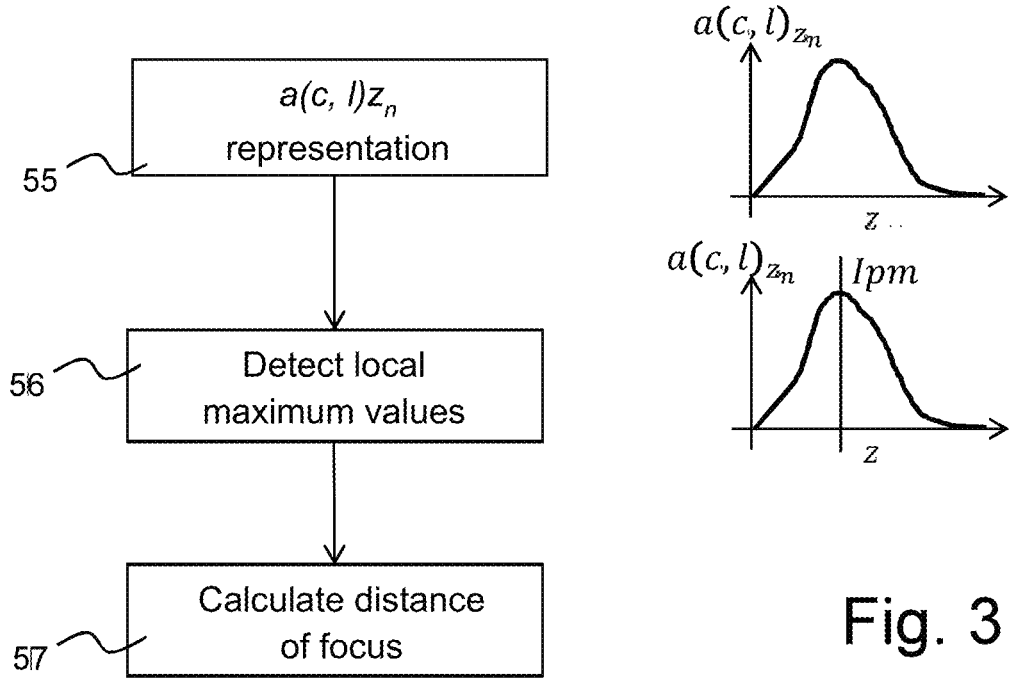

FIG. 3 illustrates an example of determination of the average focusing distance zfmoy by representing, for each coordinate (c,l), the variation of $a(c,l)_{z_n}$ according to the distance z in the image stack I1-IN. When a particle is located in the sample on the axis, parallel to the optical axis of system 23, of coordinate (c,l) in the focal plane, a variation of $a(c,l)_{z_n}$ can be observed. For example, the representation, at 55, of variations $a(c,l)_{z_n}$ is similar to a Gaussian function according to distance z. On the contrary, when no particle is present on this axis, meaning that only the middle of the sample is present, $a(c,l)_{z_n}$ does not or only very slightly varies. It is thus possible to detect, at 56, an optimum Ipm for each coordinate (c,l) representing the specific focusing distance z for this coordinate. Average focusing distance zfmoy can thus be searched for by unit 20 by calculating, at 57, the average of the distances z obtained by detecting the optimum Ipm of each coordinate (c,l). Ifmoy thus is the matrix of the series I1-IN closest to the calculated distance z. As a variation, unit 20 selects the P coordinates, for example, the 10,000 coordinates, having the largest variations of their values $a(c,l)_{z_n}$ according to z (e.g. having the largest differences between the maximum value and the minimum value), and then calculates the distance zfmoy on these P coordinates, which increases the accuracy on this distance. As a variation, the values $a(c,l)_{z_n}$ of set P are averaged, and the optimum of the curve of averaged values according to z is calculated, the distance z of the optimum being distance zfmoy.

Although the average focusing distance zfmoy illustrates a general focusing of the image, the focusing on each particle 11a-11f is not optimal, particularly due to the depth variations of particles 11a-11f with respect to one another. To improve the focusing on a specific particle 11a-11f, the disclosed embodiments provide determining an optimum focusing distance for each particle and determining a focused matrix specific to the particle. For this purpose, processing unit 20 comprises a particle identification unit 53 and a unit 54 for determining an optimal focusing distance for each identified particle and for determining the pixels of the particle for this distance.

Unit 53 of identification of the particles in matrix Ifmoy may take a plurality of shapes of image segmentation of the state of the art, such as a scanning of this matrix to detect the contours of a finite element. As a variation, unit 20 applies a prior thresholding to matrix Ifmoy, the threshold value being for example equal to Moy(Ifmoy)+p×E(Ifmoy), where Moy(Ifmoy) is the average of the pixels of matrix Ifmoy, E(Ifmoy) is their standard deviation, and p is an integer greater than 1, for example, equal to 6. The values greater than this threshold are then determined as belonging to particles, and an image segmentation is implemented on the thresholded matrix. At the end of the identification, l sets of pixel coordinates (c,l), noted Part_1, . . . , Part_i, . . . Part_I are thus obtained. Each set, stored in unit 20, lists the coordinates of the image pixels Ifmoy belonging to a same particle.

The method then determines, at 54, for each set of coordinates Part_i, which distance z provides the best focusing for the corresponding particle, and then determines what matrix in series I1-IN corresponds to this distance (or calculates a new image for this distance), and finally stores in a set Ri the pixels of the selected matrix which correspond to the coordinates listed in set Part_i.

Figure 4:
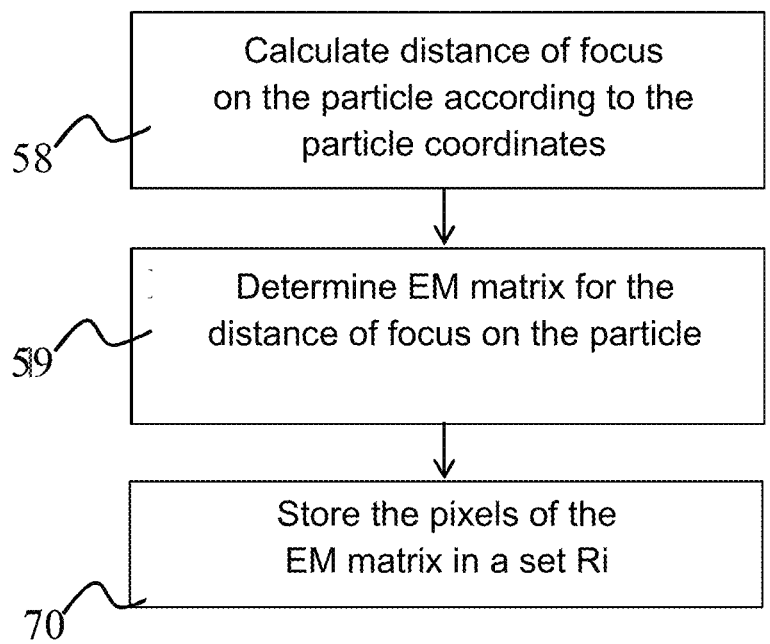

FIG. 4 illustrates an example of determination of a set Ri. Such a determination starts, at 58, by the calculation of the optimal focusing distance zfopt_i, for example, similarly to the calculation of the average focusing distance. For example, for each coordinate (c,l) of set Part_i, the distance corresponding to the optimum of $a(c,l)_{z_n}$ is calculated, after which the optimal focusing distance zfopt_i is selected to be equal to the average of the calculated distances z. As a variation, the values $a(c,l)_{z_n}$ of set Part_i are averaged, and the optimum of the curve of averaged values according to z is calculated, the distance z of the optimum being distance zfopt_i. Then, at 59, the matrix of series I1-IN corresponding to distance zfopt_i, noted I_i, is selected. At 70, the pixels of the selected matrix of coordinates listed in set Part_i are selected and stored in a set Ri.

Further, the embodiments of FIGS. 3 and 4 can be easily combined since they use the same Gaussian functions. The processings can thus be performed in parallel to limit the calculation time. The calculation time may also be decreased by sub-sampling (e.g.: in the z direction at a 0.1-μm period) the matrices of the matrix stack I1-IN enabling to select set Ri.

For each identified particle, an image Ifp_i is preferably displayed on a screen 22. This image is for example a rectangular window of the matrix I_i comprising the pixels Ri. As illustrated in the drawings, a rod bacteria effectively has the shape of a rod in the focused matrix I_i. A practitioner can thus very rapidly observe the shape of particle 11a-11f without any manipulation on optical system 23. To improve the analysis of particle 11a-11f, the latter may be represented over time via a plurality of successive acquisitions.

For this purpose, when set Ri is obtained, it is stored in a memory 21 coupled to processing unit 20. After a predefined time period, a new set Ri is searched for via a new image acquisition Ih, the time pitch being shorter than or equal to 5 minutes in the case of bacteria, and preferably shorter than or equal to 1 minute. The inventors have noted through the disclosed embodiments that this period enables to follow the phenotypic or morphological modifications of any type of bacterium. Indeed, it can be observed, by the simple visual inspection of a time series of images Ifp_i of a bacterium, that certain bacteria change from one minute to the other.

The new set Ri should correspond to the same particle 11a-11f as the first set Ri. For this purpose, unit 53 determines sets Part_1-Part_N according to the position and/or to the shape of a particle 11a-11f selected on a previous matrix Ifmoy. The focused Ifp_i sets Ri are all stored in memory 21 and screen 22 enables the practitioner to send a flow of focused images Ifp_i on a particle 11a-11f to analyze its behavior.

The device may also simultaneously perform the analysis of a plurality of samples 12, for example to perform an antibiogram of a bacterium. For this purpose, processing unit 20 may be coupled to a plurality of image sensors 16 associated with a plurality of samples 12. Processing unit 20 then processes a plurality of images Ih originating from a plurality of image sensors 16 and screen 22 illustrates the focused images Ifp.

In the embodiment which has just been described, the optimal focal distance zfopt_i corresponds to an average focusing on the particle, usual resulting in a focusing on a median plane of the particle. This particularly enables to compare sets Ri between a plurality of acquisition times. As a variation, a focusing is searched for each pixel (e.g. calculation of the distance corresponding to the optimum value of $a(c,l)_{z_n}$ according to z, search for the electromagnetic matrix at this distance, storage in set Ri of the pixel of this matrix of coordinate (c,l)), which enables to construct a 3D visualization of the particle. However, the comparison between two successive reconstructions of the particle is more difficult.

The acquisition being performed with no focus, it may be carried out at a very high frequency and, if need be, the processing may be performed after the acquisition.

Figure 5:
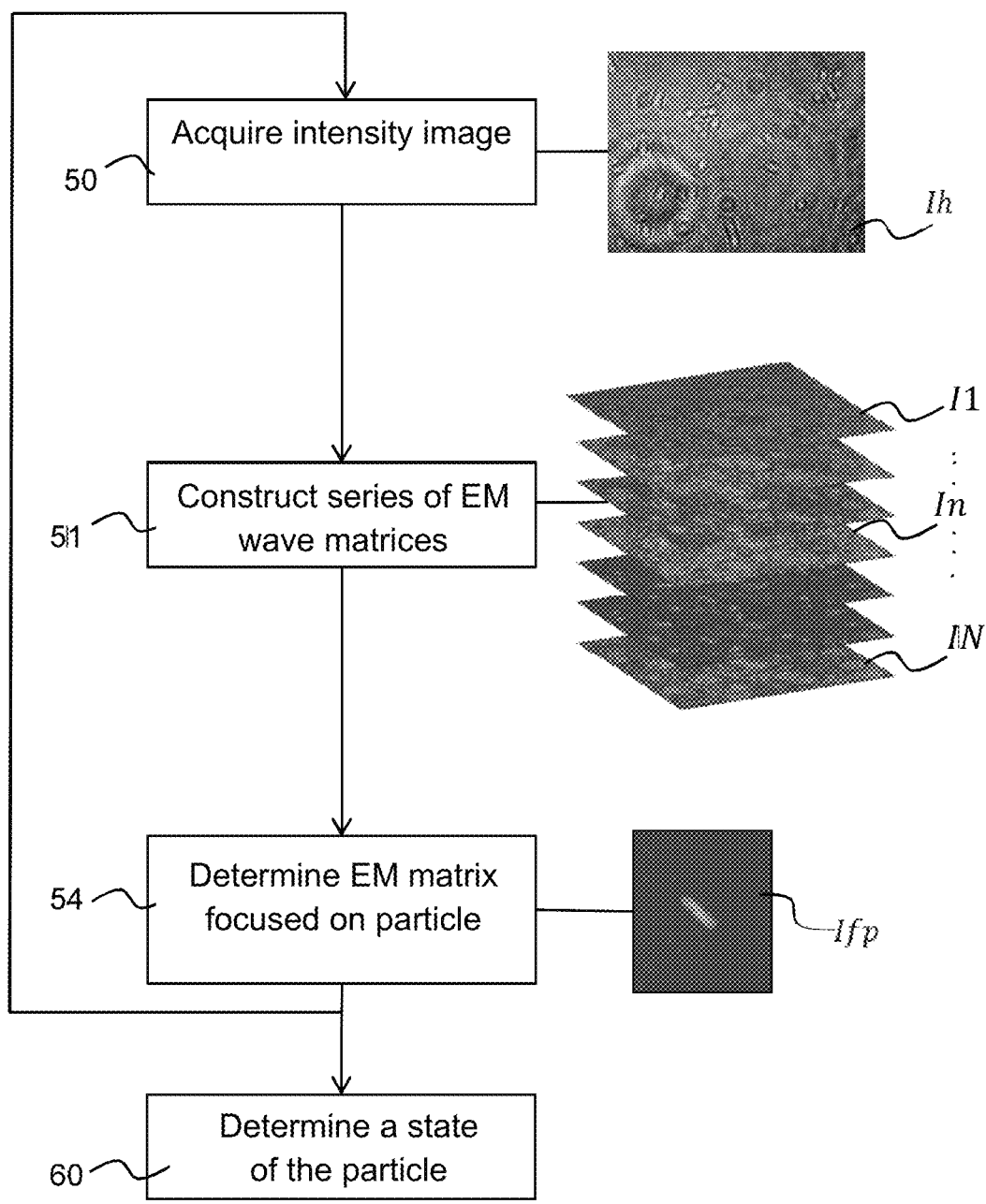

FIG. 5 illustrates a second embodiment comprising detecting the division of a microorganism over time. In this embodiment, processing unit 20 comprises a unit 60 for determining a state of particle 11a-11f according to the time variation of the set of pixels Ri associated with the microorganism, e.g. the phenotypic or morphological state of a bacterium.

In the embodiment of FIG. 5, the determination 54 of the set of pixels Ri may be performed by a simple digital focusing search from image stack I1-IN conversely to the embodiment of FIG. 2 where a double focusing search is performed. The pixels of set Ri then are those of matrix Ifmoy. As a variation, determination 54 of the set of pixels Ri may be carried out with a process similar to those of FIG. 2.

Unit 60 for determining a state of particle 11a-11f may implement different indicators and processings. For example, the state of particle 11a-11f may be analyzed according to the state of its division cycle, its morphological characteristics, its physiological characteristics or a combination of a plurality of indicators.

Preferably, the indicators are defined according to the nature of the particle 11a-11f, the state of which is searched for.

Figure 6:
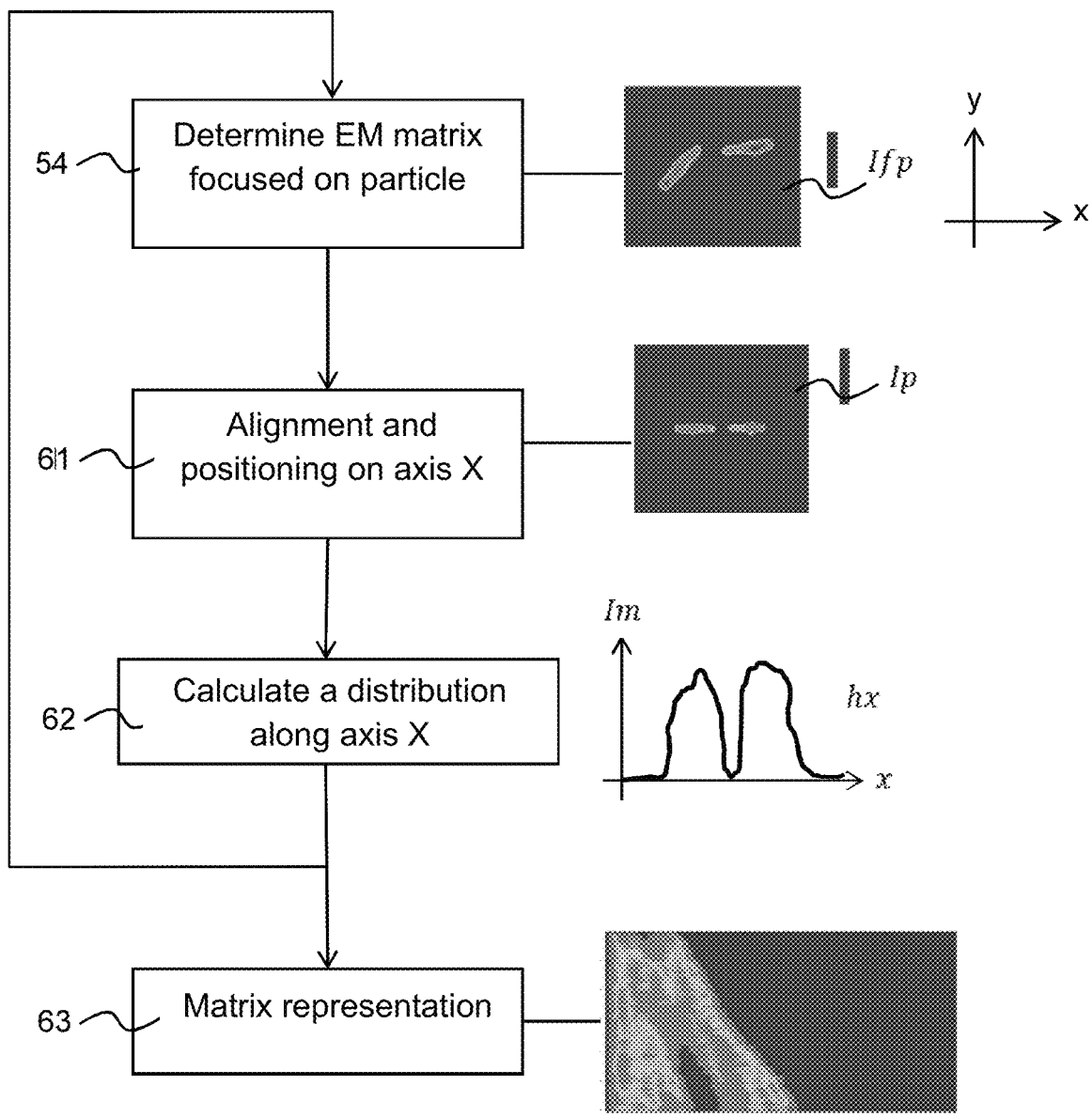

For a particle 11a-11f similar to a bacterium in the presence of an antibiotic, the embodiment of FIG. 6 is particularly efficient. In this embodiment, intensity images Ih are periodically acquired, advantageously every minute for the reasons described hereabove, and for each acquired image Ih, the set Ri associated with the bacterium is determined.

A rotation 61 is applied to set Ri to align and position particle 11a-11f on a time-invariable predefined axis, for example, by aligning on the left-hand side the particle on axis x of abscissas (i.e. the axis corresponding to the rows of the acquired images). The aligned set Ri is then projected on the alignment axis, for example, by calculating the average of the pixels on each ordinate y, (i.e. the column axis of the acquired images). The distribution Ip thus obtained is shown at 62 in the form of a distribution of sum Im per column according to the position of ordinate x of the pixels, and is for example stored in unit 20 in the form of a row vector.

The distributions are then represented over time by concatenating distributions Ip in a matrix. Noting Ip_q the distribution obtained from the q-th acquired image Ih, and Q the last acquisition time, the matrix, noted Dist_Q, can thus be written as:

$$\text{Dist\_Q} = \begin{pmatrix} \text{Ip\_1} \\ \vdots \\ \text{Ip\_q} \\ \vdots \\ \text{Ip\_Q} \end{pmatrix}$$

The matrix representation thus obtained is particularly efficient to determine the state of particle 11a-11f. For example, such a matrix representation enables to observe the lengthening of a particle or the presence of at least one cellular division.

Figure 7:
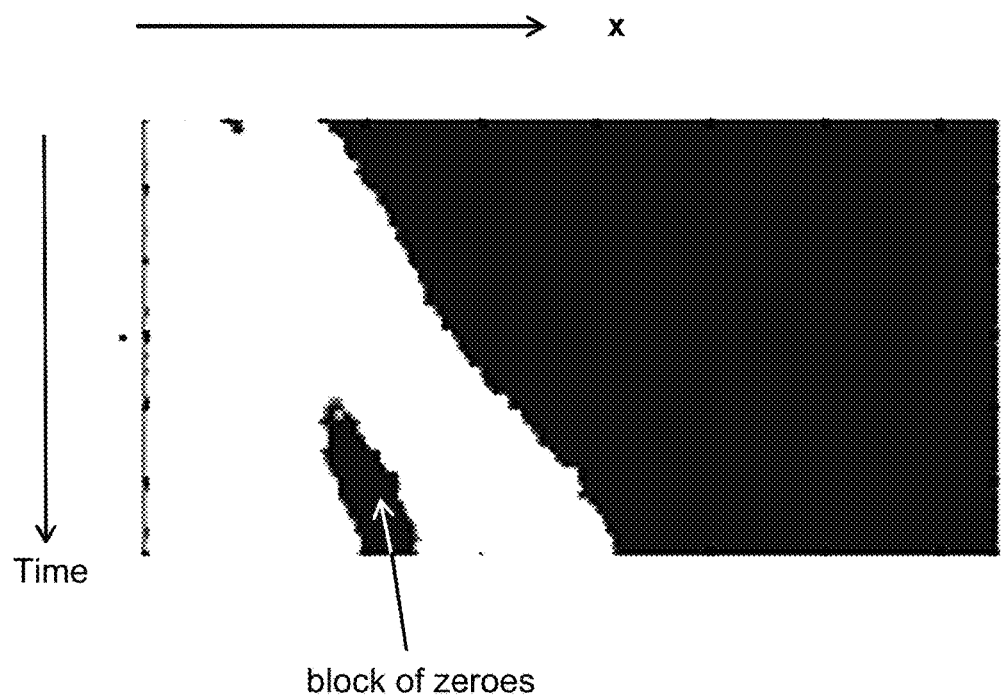
FIG. 7: a simplified representation of an image of a thresholded distribution matrix.

A simple thresholding on the shape of the matrix representation then enables to define whether an antibiotic has had an efficient action or not on a bacterium. Particularly, as illustrated in FIG. 7, one can see in the thresholded matrix, formed of zeroes and of ones, a block of zeroes surrounded with two blocks of 1, the occurrence of the block of zeroes marking the time of beginning of the division, appear and increase. The identification by processing unit 20 of the occurrence of such a block thus enables to identify in simple fashion the division of the bacterium. As a variation, other analyses may be performed by modeling the displacement speed of a particle 11a-11f between the holographic images Ih captured by image sensor 16 or by analyzing the structural characteristics of a particle 11a-11f by matching with particles of known shape.

Figure 8:
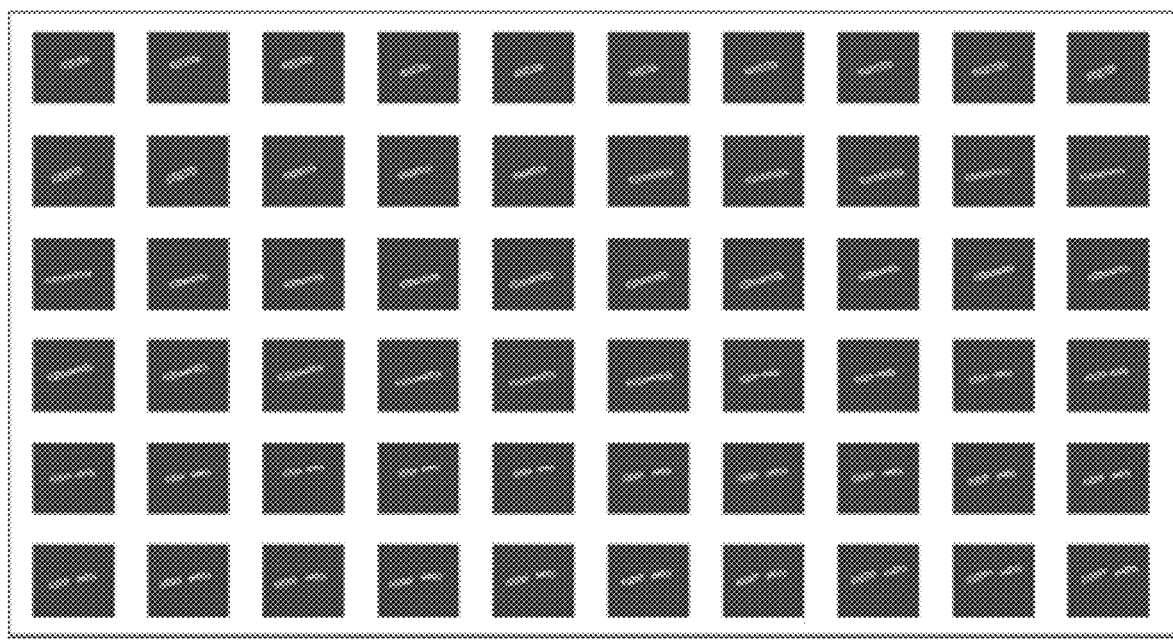
FIG. 8: a simplified representation of a set of thumbnail images comprising a bacterium observed over time due to a method according to an embodiment.
Figure 9:
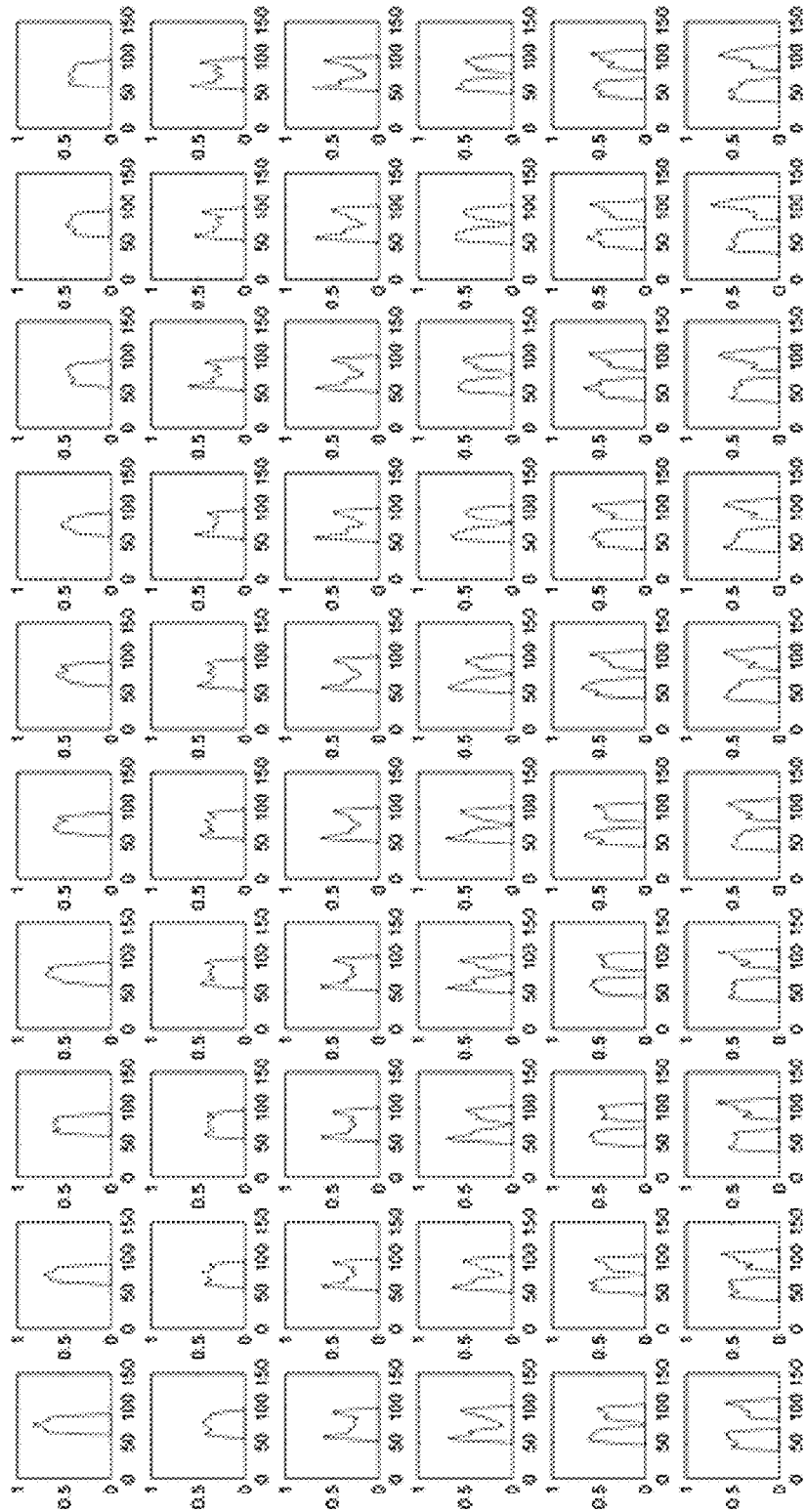
FIG. 9: a distribution set corresponding to the thumbnail images of FIG. 8.

The disclosed embodiments thus enable to obtain an accurate image of a particle 11a-11f present in a sample 12. Typically, the disclosed embodiments have enabled to obtain a thumbnail image representing a bacterium with a number of pixels in the range from 100 to 400 pixels. As a result, it is visually or digitally possible to visualize, and thus with no marking (e.g. fluorescent), the content of a microorganism. Particularly, the distribution of the intracellular material in a bacterium can be observed. Without being bound by theory, the inventors were able to observe the occurrence of two poles in a bacterium before its division, which might correspond to the meiosis of a bacterium, as illustrated in FIG. 8 which shows the time variation of a bacterium. Processing unit 20 thus implements over time a processing of set Ri of a bacterium, or of distribution Ip_q, to determine the occurrence of two areas of similar value. A division of the bacterium is thus predicted long before the division has occurred. FIG. 9 illustrates the distributions Ip_q of the bacterium illustrated in FIG. 8. As can be observed in the drawing, when the bacterium prepares for division, two poles appear in the distribution, long before the actual division, which translates as two different portions of the distribution Processing unit 20 is for example configured to detect the occurrence of two poles in the distribution and predict according to this detection the division of the bacterium, and accordingly its responsiveness to the antibiotic present in the sample.

Further, the disclosed embodiments also enable to obtain the variation of particle 11a-11f over time to visualize its behavior, for example, its displacement speed or its cellular division process.

Particularly, due to the resolution obtained by the disclosed embodiments (several hundreds of pixels per bacterium for the system designed by the inventors), it is possible to observe the influence of an antibiotic on the morphology and the intracellular content of the bacteria. Further, the high acquisition rate of the disclosed embodiments enables to very finely track along time the variations of the bacterium (e.g. growth, division, reaction to a culture medium, to a medium with an antibiotic, etc.).

An object in the air and at a distance from the sample has been described. Other types of arrangement are possible, for example, a microscopic lens immersed in a liquid tank receiving the sample and/or capable of displacing with respect to the sample.

The invention claimed is:

1. A device of acquisition of a plurality of particles present in a sample, said acquisition device comprising:
   a spatially coherent or pseudo-coherent light source directed towards a first surface of said sample;
   an optical system having an optical axis and achieving the conjugation between a plane of focus and a focal plane, directed towards a second surface of said sample opposite to said first surface, and placed relative to the sample so that the particles are not in the plane of focus;
   an image sensor placed in the focal plane of the optical system and configured to acquire an intensity image (Ih) formed by the interference between said light source and said sample; and
   a computational processing unit comprising:
      a unit of digital construction of a series of electromagnetic matrices (I1-IN) modeling, from the acquired image (Ih), an electromagnetic wave in planes parallel to the plane of focus and comprised in the sample for a plurality of offsets relative to said plane,
      a unit for determining a first electromagnetic matrix (Ifmoy) at an average distance of focus on the particles from the series of electromagnetic matrices (I1-IN);
      a unit for identifying at least one of the particles in the first electromagnetic matrix (Ifmoy) and for storing the coordinates of said particle; and
      a unit for determining a second electromagnetic matrix (Ifp) at a distance of focus on a particle identified from the components of the series of electromagnetic matrices (I1-IN) having the stored coordinates.

2. The device of acquisition of claim 1, wherein said image sensor is configured to acquire an image flow (Ih), and wherein the processing unit is configured to track a particle in the flow of first electromagnetic matrices (Ifmoy).

3. The device of acquisition of claim 2, wherein the particles are microorganisms and wherein the duration between two acquired images (Ih) originating from said image sensor is shorter than or equal to 1 minute.

4. The device of acquisition of claim 1, wherein said series of electromagnetic matrices (I1-IN) is obtained by a model of digital propagation of light through said sample, the electromagnetic matrices (I1-IN) varying by modulating a distance (z) to an optical axis of said propagation model.

5. The device of acquisition device of claim 4, wherein the processing unit comprises a unit for transforming the electromagnetic matrices originating from the propagation model by a surjective application from the complex space into the real space.

6. The device of acquisition device of claim 4, wherein the first electromagnetic matrix (Ifmoy) is obtained by representing, for each coordinate, the components at said coordinate of the electromagnetic matrices (I1-IN) according to said distance (z) to said optical axis, and by searching for an average of the maximum values of all representations.

7. The device of acquisition device of claim 5, wherein the second electromagnetic image is obtained by representing, for each coordinate of the identified particle, the components at said coordinate of the electromagnetic matrices (I1-IN) according to said distance (z) to said optical axis, and by searching for an average of the maximum values of all representations.

8. The device of acquisition of claim 1, wherein the matrices of said series of electromagnetic matrices (I1-IN) used to determine said first electromagnetic matrices (Ifmoy) and/or to determine said second electromagnetic matrix are sub-sampled according to said distance.

9. The device of acquisition device of claim 1, wherein said device comprises a plurality of acquisition units, each acquisition unit comprising an image sensor and specific focusing means, said device being configured to represent an image of a particle of each sample.

10. A method of analysis of at least one particle present in a sample, said analysis method comprising the steps of:
    emitting a spatially coherent or pseudo-coherent light source directed towards a first surface of said sample;
    acquiring by means of an image sensor an intensity image (Ih), said sensor being placed in the focal plane of an optical system having an optical axis and performing the conjugation between a plane of focus and the focal plane, directed towards a second surface of said sample opposite to said first surface, and placed relative to the sample so that the particle is not in the plane of focus, the image (Ih) being formed by interference between said light source and said sample;
    digitally constructing a series of electromagnetic matrices (I1-IN) modeling, from the acquired image (Ih), an electromagnetic wave in planes parallel to the plane of focus and comprised in the sample for a plurality of offsets with respect to said plane;

obtaining an electromagnetic matrix (Ifp) at a distance of focus on the particle from the series of electromagnetic matrices (I1-IN); and determining a state of said particle according to the electromagnetic matrix (Ifp) at the distance of focus on the particle.

11. The method of analysis of claim 10, wherein the step of obtaining the electromagnetic matrix (Ifp) at the distance of focus on the particle comprises the steps of:

determining a first electromagnetic matrix (Ifmoy) at an average distance of focus on the at least one particle from the series of electromagnetic matrices (I1-IN);

identifying a particle in the first electromagnetic matrix (Ifmoy) and storing the coordinates of said particle; and determining the electromagnetic matrix (Ifp) at a distance of focus on the particle from the components of the series of electromagnetic matrices (I1-IN) having the stored coordinates.

12. The method of analysis of claim 10, wherein said step of determining a state of said particle comprises the steps of:

rotating the electromagnetic matrix (Ifp) at the distance of focus on the particle to align the particle with a predefined axis; and calculating a distribution of the matrix aligned along said predefined axis.

13. The method of analysis of claim 10, wherein the steps of acquiring by means of an image sensor an intensity image (Ih) until the step of obtaining the electromagnetic matrix (Ifp) at the distance of focus on the particle are carried out over time for a plurality of images, the step of determining a state of said particle being carried out according to a time variation of said particle.

14. The method of analysis of claim 13, wherein said step of determining a state of said particle comprises the steps of:

rotating for each acquired image, the electromagnetic matrix at the distance of focus (Ifp) on the particle to align the particle with a predefined axis;

calculating for each acquired image, a distribution of the matrix aligned along said predefined axis; and creating a matrix representation of the distributions associated with each image over time.

15. The method of analysis of claim 10, wherein said step of determining a state of said particle is carried out according to a division state of said particle.

16. The method of analysis of claim 10, wherein said step of determining a state of said particle is carried out according to a morphological characteristic of said particle.

17. The method of analysis of claim 10, wherein said step of determining a state of said particle is carried out according to a physiological characteristic of said particle.

18. The method of analysis of claim 10, wherein said particle corresponds to a bacterium and said sample integrates an antibiotic.

* * * * *